US010215767B2

United States Patent
Aster et al.

(10) Patent No.: US 10,215,767 B2
(45) Date of Patent: Feb. 26, 2019

(54) METHOD OF DETECTING PLATELET ACTIVATING ANTIBODIES THAT CAUSE HEPARIN-INDUCED THROMBOCYTOPENIA/THROMBOSIS

(71) Applicant: Blood Center Research Foundation, Milwaukee, WI (US)

(72) Inventors: Richard H. Aster, Milwaukee, WI (US); Daniel W. Bougie, Germantown, WI (US); Curtis Gerald Jones, Milwaukee, WI (US); Anand Padmanabhan, Oconomowoc, WI (US)

(73) Assignee: Versiti Blood Research Institute Foundation, Inc., Milwaukee, WI (US)

( * ) Notice: Subject to any disclaimer, the term of this patent is extended or adjusted under 35 U.S.C. 154(b) by 0 days.

(21) Appl. No.: 15/818,128

(22) Filed: Nov. 20, 2017

(65) Prior Publication Data
US 2018/0074078 A1 Mar. 15, 2018

Related U.S. Application Data

(63) Continuation of application No. 14/437,066, filed as application No. PCT/US2014/062591 on Oct. 28, 2014, now Pat. No. 9,851,367.
(Continued)

(51) Int. Cl.
*G01N 33/86* (2006.01)
*C12Q 1/56* (2006.01)
(Continued)

(52) U.S. Cl.
CPC ............... *G01N 33/86* (2013.01); *C12Q 1/56* (2013.01); *G01N 33/56966* (2013.01);
(Continued)

(58) Field of Classification Search
CPC ............ G01N 33/86; G01N 33/56966; G01N 33/6854; G01N 2800/222;
(Continued)

(56) References Cited

U.S. PATENT DOCUMENTS 5,763,201 A 6/1998 Tomer
7,790,362 B2 9/2010 Coller et al.
(Continued)

FOREIGN PATENT DOCUMENTS

EP 2330128 A1 6/2011
WO 2013/042111 A2 3/2013

OTHER PUBLICATIONS

Amiral, et al., Platelet Factor 4 Complexed to Heparin is the Target for Antibodies Generated in Heparin-Induced Thrombocytopenia, Thrombosis and Haemostasis, 1992, 68(1):95-96.
(Continued)

*Primary Examiner* — Gailene Gabel
(74) *Attorney, Agent, or Firm* — Quarles & Brady LLP

(57) ABSTRACT

The present invention provides a method of detecting platelet activation in a patient, the method comprising the steps of a) obtaining a blood sample from a patient suspected of having heparin-induced thrombocytopenia (HIT); b) incubating an effective amount of platelet factor 4 (PF4) with a sample of platelets to yield a sample of PF4-treated platelets; c) contacting the patient blood sample with the PF4-treated platelets; and d) measuring the extent of platelet activation, wherein an increase in platelet activation compared with results obtained using a normal blood sample is indicative of the patient having HIT.

7 Claims, 4 Drawing Sheets

Related U.S. Application Data

(60) Provisional application No. 61/896,951, filed on Oct. 29, 2013.

(51) Int. Cl.
*G01N 33/569* (2006.01)
*G01N 33/68* (2006.01)

(52) U.S. Cl.
CPC .................. *G01N 33/6854* (2013.01); *G01N 2333/70564* (2013.01); *G01N 2800/222* (2013.01); *G01N 2800/224* (2013.01); *G01N 2800/226* (2013.01)

(58) Field of Classification Search
CPC ....... G01N 2800/224; G01N 2800/226; G01N 2333/70564; C12Q 1/56
See application file for complete search history.

(56) References Cited

U.S. PATENT DOCUMENTS

| | | | |
|---|---|---|---|
| 8,574,828 B2 | 11/2013 | Coller et al. | |
| 2007/0190582 A1* | 8/2007 | Poncz ................. | G01N 33/5023 435/7.21 |
| 2014/0038207 A1 | 2/2014 | Tomer | |

OTHER PUBLICATIONS

Arepally, et al., Heparin-Induced Thrombocytopenia, Annu. Rev. Med., 2010, 61:77-90.
Bakchoul, et al., Performance Characteristics of Two Commercially Available IgG-specific Immunoassays in the Assessment of Heparin-Induced Thrombocytopenia (HIT), Thrombosis Research, 2011, 127:345-348.
Bougie, et al., Drug-Dependent Clearance of Human Platelets in the NOD/scid Mouse by Antibodies form Patients with Drug-Induced Immune Thrombocytopenia, Blood, 2010, 116(16):3033-3038.
Bougie, et al., Antibodies Causing Thrombocytopenia in Patients Treated with RGD-mimetic Platelet Inhibitors Recognize Ligand-Specific Conformers of alphaIIb/beta3 Integrin, Blood, 2012, 119(26):6317-6325.
Cuker, et al., How I Treat Heparin-Induced Thrombocytopenia, Blood, 2012, 119(10):2209-2218.
Cuker, et al., Novel Diagnostic Assays for Heparin-Induced Thrombocytopenia, Blood, 2013, 121(18):3727-3732.
Davoren, et al., Heparin-Induced Thrombocytopenia and Thrombosis, American Journal of Hematology, 2006, 81:36-44.
Go, et al., Heart Disease and Stroke Statistics—2013 Update—A Report from the American Heart Association, Circulation, 2013, 127:e6-e245.
Greinacher, et al., Heparin-Associated Thrombocytopenia: Isolation of the Antibody and Characterization of a Multimolecular PF4-Heparin Complex as the Major Antigen, Thrombosis and Haemostasis, 1994, 71(2):247-251.
Greinacher, et al., Heparin-Induced Thrombocytopenia: A Prospective Study on the Incidence, Platelet-Activating Capacity and Clinical Significance of Antiplatelet Factor 4/heparin Antibodies of the IgG, IgM, and IgA Classes, Journal of Thrombosis and Haemostasis, 2007, 5:1666-1673.
Horne III, et al., Platelet Binding of IgG from Patients with Heparin-Induced Thrombocytopenia, J. Lab. Clin. Med., 1996, 127:435-442.
Horne III, et al., Simultaneous Binding of Heparin and Platelet Factor-4 to Platelets: Further Insights Into the Mechanism of Heparin-Induced Thrombocytopenia, American Journal of Hematology, 1998, 58:24-30.
Jang, et al., When Heparins Promote Thrombosis, Review of Heparin-Induced Thrombocytopenia, Circulation, 2005, 111:2671-2683.

Juhl, et al., Incidence and Clinical Significance of Anti-PF4/Heparin Antibodies of the IgG, IgM, and IgA Class in 755 Consecutive Patient Samples Referred for Diagnostic Testing for Heparin-Induced Thrombocytopenia, Eur. J. Haematol., 2006, 76:420-426.
Kelton, et al., Immunoglobulin G From Patients With Heparin-Induced Thrombocytopenia Binds to a Complex of Heparin and Platelet Factor 4, Blood, 1994, 11:3232-3239.
Kowalska, et al., Role of the Platelet Chemokine Platelet Factor 4 (PF4) in Hemostasis and Thrombosis, Thrombosis Research, 2010, 125(4):292-296.
Kowalska, et al., Antibodies Associated with Heparin-Induced Thrombocytopenia (HIT) Inhibit Activated Protein C Generation: New Insights into the Prothrombotic Nature of HIT, Blood, 2011, 118(10):2882-2888.
Levine, Finding Haystacks Full of Needles—From Opus to Osler, Chest, 2005, 127:1488-1490.
Lo, et al., What is the Potential for Overdiagnosis of Heparin-Induced Thrombocytopenia?, Am. J. Hematol., 2007, 82:1037-1043.
McFarland, et al., Improving the Specificity of the PF4 ELISA in Diagnosing Heparin-Induced Thrombocytopenia, Am. J. Hematol., 2012, 87:776-781.
Morel-Kopp, et al., Heparin-Induced Thrombocytopenia: Evaluation of IgG and IgGAM ELISA Assays, International Journal of Laboratory Hematology, 2011, 33:245-250.
Nazi, et al., FcgammaRIIa Proteolysis as a Diagnostic Biomarker for Heparin-Induced Thrombocytopenia, Journal of Thrombosis and Haemostasis, 2013, 11:1146-1153.
Nazi, et al., Distinguishing Between Anti-PF4/Heparin Antibodies That Can and Cannot Cause Heparin-Induced Thrombocytopenia, 'Accepted Article', doi: 10.1111/jth.13066, Jul. 20, 2015.
Newman, et al., Heparin-Induced Thrombocytopenia: New Evidence for the Dynamic Binding of Purified Anti-PF4-Heparin Antibodies to Platelets and the Resultant Platelet Activation, Blood, 2000, 96:182-187.
Poncz, et al., The Role of Surface PF4:Glycosaminoglycan Complexes in the Pathogenesis of Heparin-Induced Thrombocytopenia (HIT), Journal of Pathophysiology of Haemostasis and Thrombosis, 2006, 35(1-2):46-49.
Rauova, et al., Role of Platelet Surface PF4 Antigenic Complexes in Heparin-Induced Thrombocytopenia Pathogenesis: Diagnostic and Therapeutic Implications, Blood, 2006, 107:2346-2353.
Rauova, et al., Platelet and Monocyte Antigenic Complexes in the Pathogenesis of Heparin-Induced Thrombocytopenia (HIT), Journal of Thrombosis and Haemostasis, 2009, 7(Suppl 1):249-252.
Rauova, et al., Monocyte-Bound PF4 in the Pathogenesis of Heparin-Induced Thrombocytopenia, Blood, 2010, 116 (23):5021-5031.
Sachais, et al., Dynamic Antibody-Binding Properties in the Pathogenesis of HIT, Blood, 2012, 120(5):1137-1142.
Shantsila, et al., Heparin-Induced Thrombocytopenia, Chest, 2009, 135:1651-1664.
Sheridan, et al., A Diagnostic Test for Heparin-Induced Thrombocytopenia, Blood, 1986, 67(1):27-30.
Suh, et al., Antibodies from Patients with Heparin-Induced Thrombocytopenia/Thrombosis Recognize Different Epitopes on Heparin: Platelet Factor 4, Blood, 1998, 91(3):916-922.
Suvarna, et al., PF4/Heparin Complexes are T Cell-Dependent Antigens, Blood, 2005, 106:929-931.
Visentin, et al., Antibodies from Patients with Heparin-Induced Thrombocytopenia / Thrombosis are Specific for Platelet Factor 4 Complexed with Heparin or Bound to Endothelial Cells, J. Clin. Invest., 1994, 93:81-88.
Warkentin, et al., Heparin-Induced Thrombocytopenia in Patients Treated with Low-Molecular-Weight Heparin or Unfractionated Heparin, The New England Journal of Medicine, 1995, 332:1330-1335.
Warkentin, How I Diagnose and Manage HIT, Hematology, 2011, pp. 143-149.
Zou, et al., Receiver-Operating Characteristic Analysis for Evaluating Diagnostic Tests and Predictive Models, Circulation, 2007, 115:654-657.
International Search Report and Written Opinion dated Jan. 13, 2015 in connection with PCT/US2014/062591.
European Patent Office, Extended European Search Report, Application No. 14857347.0, dated Feb. 28, 2017.

* cited by examiner

METHOD OF DETECTING PLATELET ACTIVATING ANTIBODIES THAT CAUSE HEPARIN-INDUCED THROMBOCYTOPENIA/THROMBOSIS

CROSS REFERENCE TO RELATED APPLICATIONS

This application is a continuation of U.S. application Ser. No. 14/437,066, filed Apr. 20, 2015, which represents the national stage entry of PCT/US2014/062591, filed Oct. 28, 2014, which claims priority to U.S. Provisional Application No. 61/896,951, filed Oct. 29, 2013, each of which are incorporated by reference for all purposes.

STATEMENT REGARDING FEDERALLY SPONSORED RESEARCH

This invention was made with government support under grant HL-13629 awarded by the National Institutes of Health. The government has certain rights in the invention.

BACKGROUND

Heparin is a highly sulfated glycosaminoglycan (GAG) consisting of repeating disaccharide units. Unfractionated heparin has an average molecular weight of 12-15 kilodaltons (kD). Most heparin prepared commercially for infusion into human patients is isolated from the gut mucosa of pigs in the form termed "unfractionated heparin" (UFH). Fractionation of UFH by various methods results in low molecular weight heparin (LMWH) with 60% of the polysaccharide chains having a molecular weight less than 8 kD. The anticoagulant affect of UFH is mediated by its interaction with anti-thrombin three (ATIII), a serine protease inhibitor of thrombin.

Binding of UFH to anti-thrombin markedly increases inhibition by ATIII of the coagulation proteases, thrombin and Factor Xa. It is estimated that in the United States alone, about one third of hospitalized patients or 12 million patients per year undergoing surgery and other therapeutic procedures are given UFH or LMWH for treatment or prevention of thrombosis. About 1-5% of these patients develop the disorder "heparin-induced thrombocytopenia" (HIT).

HIT is an adverse reaction to heparin, in which affected patients produce platelet-activating antibodies and develop thrombocytopenia. A subset of these individuals experience arterial or venous thrombosis, which in severe cases can be life-threatening. Experts believe that up to 600,000 people per year develop HIT, which is double the number of breast cancer cases diagnosed annually and nearly equal to the number of new cases of angina diagnosed each year in the United States. Because early diagnosis and treatment can reduce morbidity, it is important that a timely and accurate diagnosis of HIT be made. An accurate diagnosis of HIT requires attention to both clinical findings and laboratory test results.

Conventional treatment for patients suspected of having HIT includes the immediate cessation of all heparin followed by prompt administration of a non-heparin, alternative anticoagulant such as a direct thrombin inhibitor. Such treatments involve additional hospitalization, a considerable expense, and a risk of severe bleeding of 1% per day. Thus, an accurate diagnosis of HIT and characterization of thrombosis risk is critical for effective patient management.

Platelet factor 4 (PF4) is a 32 kD tetrameric protein consisting of four identical 70-amino acid subunits that is released from the alpha-granules of activated platelets and binds with high affinity to heparin, leading to generation of the PF4 epitopes that HIT antibodies recognize. One physiologic role of PF4 may be neutralization of heparin-like molecules on the endothelial surface of blood vessels, thereby promoting coagulation. Other roles appear to include pro-inflammatory activity, inhibition of angiogenesis, and inhibition of megakaryocyte proliferation and platelet production.

HIT is caused by antibodies that recognize PF4 in a complex with heparin. Among available tests for HIT antibody detection, the serotonin release assay (SRA) is considered by many to correlate best with a clinical picture typical of HIT and is often used as a surrogate for HIT diagnosis. However, the SRA is performed routinely only in a few specialized laboratories because of challenges that include the use of radioactivity, labor intensiveness, reliance on fresh platelets, and technical demands of the assay. An alternative, widely used diagnostic test, the PF4-based ELISA, is technically simple and highly sensitive for antibody detection but lacks the necessary specificity to diagnose clinical HIT.

Other recently developed HIT assays show promise but are still investigational and not yet validated for clinical use. It remains unclear why some Heparin-PF4 directed antibodies cause HIT but many others do not. It is generally agreed, however, that antibodies testing positive in the SRA are most likely to be pathogenic and to cause thrombocytopenia as well as thrombosis, the most serious complication of HIT.

Accordingly, there is a need for assays that distinguish between antibodies that activate platelets and those that do not and can be performed in a relatively short time by a typical hospital laboratory.

BRIEF SUMMARY OF THE INVENTION

The present invention provides a method of detecting platelet-activating antibodies in a patient, the method comprising the steps of a) obtaining a blood sample from a patient suspected of having heparin-induced thrombocytopenia (HIT); b) incubating an effective amount of platelet factor 4 (PF4) with a sample of platelets to yield a sample of PF4-treated platelets; c) contacting the patient blood sample with the PF4-treated platelets; and d) measuring platelet activation in the patient blood sample, wherein an increase in platelet activation relative to a normal sample is indicative of the patient having HIT.

In general, the platelets most suitable and practical for use in the method would be washed normal donor platelets. However, abnormal platelets, unwashed platelets, isolated platelets, purified platelets, or platelet derivatives could be used. In general, a readout can be considered positive when the ratio of the signal obtained with patient sample exceeds the signal obtained using normal sample by at least 2 fold and most preferably at least 3 fold. In a first example, an increase in p-selectin median fluorescence intensity (MFI) of >8000 relative to normal serum may be considered positive in the assay depicted in FIG. 1. For best results, validation using an appropriate number of true positive and true negative control samples should be performed to define appropriate cutoffs for positive versus negative samples.

In one embodiment, the method of the present invention occurs in the absence of heparin, but in alternate embodiments, contacting the patient sample with the PF4-treated platelets may occur in the presence of added heparin or a heparin-like compound in amounts ranging from 0.05 to 100 units/ml.

The present invention also provides a method of detecting platelet-activating (pathogenic) HIT antibodies by evaluating platelet-binding antibodies in a patient, the method comprising the steps of a) obtaining a blood sample from a patient suspected of having heparin-induced thrombocytopenia (HIT); b) incubating an effective amount of platelet factor 4 (PF4) with a sample of platelets to yield a sample of PF4-treated platelets; c) contacting the patient blood sample with the PF4-treated platelets; and d) measuring the amount of platelet-binding antibodies in the patient blood sample, wherein the presence of such antibodies, detected by evaluation of antibody binding to platelets in patient sample as compared to normal sample, is indicative of the patient having HIT. In general, a readout can be considered positive when the ratio of signal (in this case Ig-platelet binding) obtained with patient sample exceeds the signal obtained using normal sample by at least 2 fold and most preferably at least 3 fold. In the assay depicted in FIG. 2, a sample is considered positive if it demonstrates an increase in median fluorescence intensity (MFI) of >2500 relative to normal serum, and an increase in MFI of 80%.

The invention also provides a kit for determining the presence of platelet-activating antibodies in a patient sample. In one embodiment the kit comprises: a) an effective amount of purified human PF4; b) an effective amount of at least two labeled anti-human antibodies, one reactive with a platelet-specific marker such as CD41 and the other reactive with a marker selected as a measure of platelet activation such as p-selectin; c) an effective amount of high-dose heparin sufficient to confirm specificity of a positive reaction; d) an effective amount of a positive control HIT antibody; e) an effective amount of a negative control sample; f) instructions for obtaining platelets for use in the assay; g) instructions for performing the assay; h) one or more additional reagents such as fluorescent-labeled annexin V or anti-p-selectin antibody to detect markers of platelet activation and g) prostaglandin E1 to minimize baseline platelet activation. In another embodiment the kit comprises: a) an effective amount of purified human PF4; b) an effective amount of at least one labeled anti-human antibody to measure platelet activation such as anti-human p-selectin; and c) instructions for performing the assay.

BRIEF DESCRIPTION OF THE DRAWINGS

FIG. 1A Left. When no exogenous PF4 was preincubated with platelets, SRA+ samples (n=29) produced only a slight increase in p-selectin expression; SRA- samples (n=24) had little effect. Values shown on the ordinate depict the difference between median fluorescence intensity (MFI) (a measure of p-selectin expression) obtained using patient serum and MFI obtained with pooled normal serum. Platelet-specific events are gated based on CD41 (GpIIb) positivity with the use of an Alexa Fluor 647-labeled GpIIb specific antibody.

FIG. 1A Center. When exogenous PF4 was preincubated with platelets, all SRA+(SRA positive) samples produced high levels of p-selectin expression and were clearly distinguishable from SRA- (SRA negative) samples.

FIG. 1A Right. When high-dose heparin (HD UFH) was added, p-selectin expression was significantly decreased such that SRA+ samples exhibited only a slight increase in p-selectin expression relative to SRA- samples.

FIG. 1B. Receiver operating characteristic (ROC) curves were constructed using SRA as the disease classifying variable (i.e., a positive p-selectin expression assay in an SRA+ sample would denote a "true positive"). The area under the curve (AUC) for the PF4-fortified p-selectin assay was 1.0, demonstrating that this assay had perfect diagnostic accuracy for the samples tested. SRA was performed at least twice on each sample, and all results were consistent between runs in the samples used in this study (24 SRA-, and 29 SRA+). Horizontal bars depict the mean of each group. Asterisks indicate significance of the difference between means [$p<0.0001$ (**), $p<0.001$ (*)].

FIG. 2A Left. When no exogenous PF4 was preincubated with platelets, SRA+ samples (n=29) produced only a slight increase in IgG binding to platelets relative to normal serum; SRA- samples (n=24) had little effect. Ordinate depicts the difference between MFI (a measure of IgG binding) obtained with patient serum and MFI obtained with pooled normal serum. Platelet-specific events are gated based on CD41 (GpIIb) positivity with the use of an Alexa Fluor 647-labeled CD41-specific antibody.

FIG. 2A Center. When exogenous PF4 was preincubated with platelets, SRA+ samples produced significantly higher levels of IgG binding than SRA- samples.

FIG. 2A Right. When high-dose heparin (HD UFH) was added, IgG-platelet binding was markedly decreased, such that SRA+ samples could not be differentiated from SRA- samples.

FIG. 2B. Receiver operating characteristic (ROC) curves were constructed using SRA as the disease classifying variable (i.e., a positive IgG-platelet binding assay in an SRA+ sample would denote a "true positive"). Using the experimental conditions outlined here, a combinatorial strategy in which a sample is considered positive if it demonstrates an increase in median fluorescence intensity (MFI) of >2500 relative to normal serum, and an increase in MFI of 80% with addition of PF4 (to exclude antibody binding to platelets due to HLA antibodies) results in near perfect accuracy in discriminating between SRA+ and SRA-HIT antibodies (AUC=0.94). This demonstrates that this assay had a high level of diagnostic accuracy in the samples tested. SRA was performed at least twice on each sample, and all results were consistent between runs in the samples used in this study (24 SRA-, and 29 SRA+). Horizontal bars depict the mean of each group. Asterisks indicate significance of the difference between means [$p<0.0001$ (****), $p<0.05$ (*)].

DETAILED DESCRIPTION OF THE INVENTION

I. In General

Figure 1A:
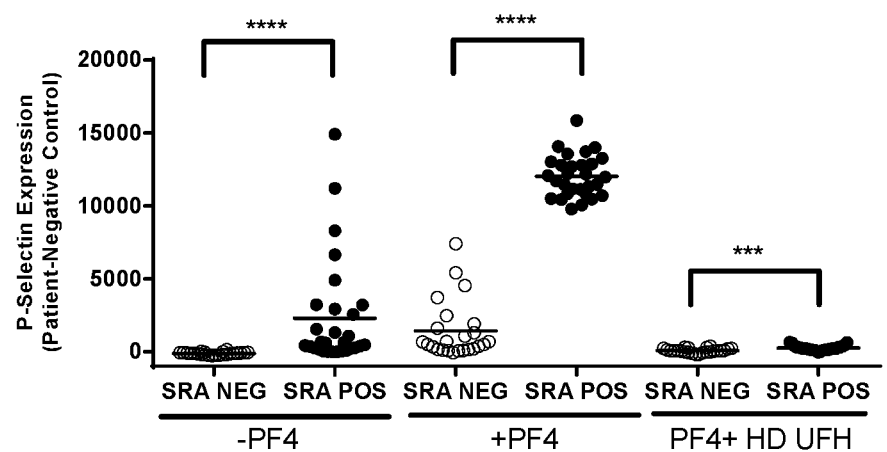
FIGS. 1A-1B. Accurate detection of platelet-activating (SRA+) patient samples in the p-selectin expression assay.

In the specification and in the claims, the terms "including" and "comprising" are open-ended terms and should be interpreted to mean "including, but not limited to . . . ." These terms encompass the more restrictive terms "consisting essentially of" and "consisting of"

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

II. The Invention

In one embodiment, the invention provides a method of detecting platelet-activating (pathogenic) HIT antibodies in a patient suspected of having HIT to aid in the diagnosis of HIT. The method of the present invention detects patient antibodies that are capable of activating platelets that have been pre-incubated with PF4. One can also add platelets, patient sample and PF4 together at the same time and then detect the level of platelet activation however, pre-incubation of platelets with PF4 gives maximum platelet activation for some patient samples and is the preferred embodiment. The use of exogenous PF4 and the lack of a requirement for heparin are unique features of the claimed method. The method of the present invention enables the simple, rapid and sensitive detection of antibodies that increase the risk of thrombosis/thrombocytopenia in a patient treated with heparin.

In one embodiment, the method comprises a) obtaining a serum or plasma sample from a patient suspected of having HIT; b) incubating an effective amount of platelet factor 4 (PF4) with washed normal donor platelets at room temperature for 20 minutes to yield a sample of PF4-treated platelets; c) contacting the patient blood sample to the sample of PF4-treated platelets at room temperature for 60 minutes; and d) measuring the amount of platelet-activating antibodies in the patient blood sample, wherein the presence of pathogenic HIT antibodies detected by evaluation of platelet activation by patient sample as compared to activation by normal serum is indicative of the patient having HIT. An increase in p-selectin median fluorescence intensity (MFI) of >8000 relative to normal serum may be considered positive in the assay depicted in FIG. 1. In general, a readout can be considered positive when the ratio of signal (in this case p-selectin expression) obtained with patient sample exceeds the signal obtained using normal sample by at least 2 fold and most preferably at least 3 fold.

In one embodiment, the amount of platelet-activating antibodies in the patient sample is determined by measuring one or more markers of platelet activation, including but not limited to, an increase in platelet surface p-selectin; an increase in binding of annexin V to the platelet surface; an increased release of serotonin, beta thromboglobulin, pyrophosphate, fibronectin or von Willebrand factor from the platelets; an increased proteolytic cleavage of the platelet membrane protein Fc gamma RII (CD32); a change in platelet shape; or an increased level of ionized calcium in the platelet cytoplasm. The amount of platelet activation in the patient sample may also be determined by measuring changes in expression levels of one or more CD markers found on activated platelets; platelet aggregation; intracellular calcium levels; integrin conformation; release of platelet granule contents such as serotonin, ATP, ADP, or VWF; platelet membrane potential; or platelet impedance.

Figure 2A:
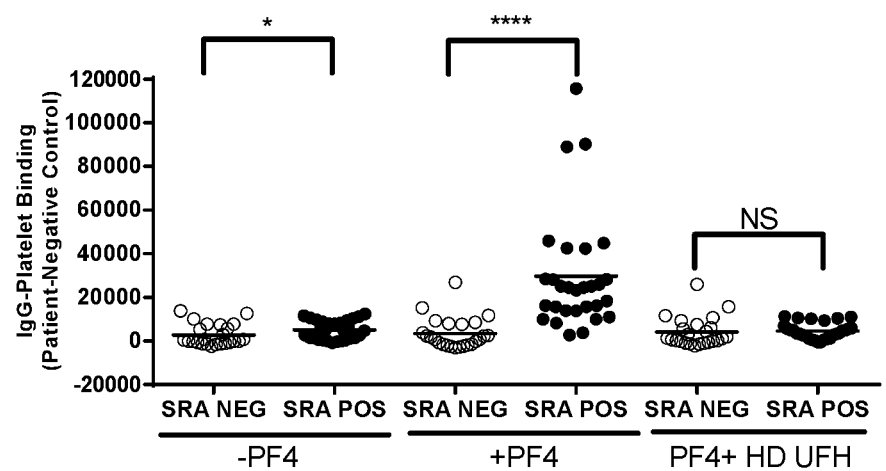
FIGS. 2A-2B. Accurate detection of platelet-activating (SRA+) patient samples in the IgG-platelet binding assay.

FIGS. 1A and 2A provide concrete examples of detection of platelet-activating antibodies using p-selectin expression and IgG binding as endpoints. Measurements encompass various things that can be useful in detecting platelet activation under special conditions, using conventional methods known to those of skill in the art. Our discovery is of the usefulness of detecting platelet activating antibodies by virtue of their ability to activate platelets treated with PF4. We have shown two such examples of assays that can detect this platelet activation, but others could be used.

In one embodiment, measuring platelet-activating (pathogenic) HIT antibodies in a patient sample is performed by measuring human immunoglobulin binding to platelets.

In one embodiment, a high-dose heparin control, where heparin is present at a level of at least 50 U/ml, demonstrates that the reaction decreases to baseline levels, proving that platelet activation was specifically mediated by HIT antibodies.

In another embodiment, the method of the present invention may be performed in the presence of low-dose heparin, heparin-like molecules or polyanionic compounds, although these substances are not required to measure the amount of platelet-activating antibodies. The addition of low-dose heparin in the assay appears to have no measurable effect on improving the sensitivity or specificity of the claimed assay.

In another embodiment, the amount of platelet-activating antibodies may be measured by observing increased platelet aggregation or agglutination by one of many methods known to one of skill in the art.

In one embodiment, the method of the present invention may further comprise a fluorescence activated cell sorting (FACS) assay adding two or more fluorescently labeled antibodies. In one embodiment, one antibody is specific for a platelet-specific marker such as CD41 and another antibody is specific for a surface marker of platelet activation such as anti-p-selectin antibody or the combination of annexin V binding and anti-annexin V antibody to detect that binding.

In one embodiment, the method of the present invention may further comprise a fluorescence activated cell sorting (FACS) assay adding a fluorescently labeled probe specific for a surface marker of platelet activation such as anti-p-selectin antibody, the combination of annexin V binding and labeled anti-annexin V antibody to detect that binding, or the use of directly labeled annexin V.

In another embodiment, the method of the present invention comprises a method of detecting platelet-activating (pathogenic) HIT antibodies by measuring platelet-binding antibodies in a patient. The method comprises a) obtaining a patient blood sample from a patient suspected of heparin-induced thrombocytopenia (HIT); b) incubating an effective amount of platelet factor 4 (PF4) with a sample of platelets to yield a sample of PF4-treated platelets; c) contacting the patient blood sample with the PF4-treated platelets; and d) measuring the amount of platelet-binding antibodies in the patient blood sample, wherein the presence of pathogenic HIT antibodies detected by evaluation of antibody binding to platelets in patient sample as compared to platelet binding antibodies in normal serum is indicative of the patient having HIT.

In one embodiment, the antigen used to mark platelets for flow cytometric analysis is CD9, CD23, CD31, CD36, CD41, CD42, CD49, CD61, CD62 P, CD63, CD107, CD151, CD165 their isoforms, or any marker present on the outside of platelets. Platelets can also be identified in flow cytometry by their forward and side-scatter properties.

Specifically, in one embodiment, we measure the amount of platelet activation in a patients blood sample where the patient is suspected of having HIT. Step one is pre-incubating platelets with PF4; step two is incubating a patient sample with the PF4-treated platelets to allow them to become activated; step three is measuring platelet activation by looking at a rise in CD62P expression as compared to a normal sample. An increase in platelet activation is indicative of the patient having HIT. This occurs because alpha granules expressing high levels of CD62P inside the platelets migrate to the surface and fuse in order to spill their contents into the bloodstream. This causes the rise of CD62P on the surface of the activated platelets.

In one embodiment, measuring the amount of platelet-binding antibodies in the patient blood sample comprises measuring the amount of patient antibodies that bind to PF4-treated platelets and comparing that value with the amount of antibody that binds when a normal blood sample is used. In the assay depicted in FIG. 2, a sample is considered positive if it demonstrates an increase in median fluorescence intensity (MFI) of >2500 relative to normal serum. In general, a readout can be considered positive when the ratio of signal (in this case Ig-platelet binding) obtained with patient sample exceeds the signal obtained using normal sample by at least 2 fold and most preferably at least 3 fold. In this embodiment, detection of patient antibodies that bind to platelets that have been pre-treated with PF4 is indicative of HIT. In this embodiment, platelets are pre-treated with PF4 and then incubated with the patient blood sample. The platelets are washed once and the quantity of platelet-bound antibody is measured by adding, for example, a fluorescent-labeled secondary antibody specific for human immunoglobulin G, A or M.

Kits. The invention also provides a kit for determining the presence of platelet-activating antibodies in patient serum. In one embodiment the kit comprises: a) an effective amount of purified human PF4; b) an effective amount of at least one labeled anti-human antibody for markers of platelet activation, or if two are used, one could be a platelet-specific antibody such as anti-CD41 and the other reactive with a marker of platelet activation such as p-selectin; c) an effective amount of high-dose heparin sufficient to confirm specificity of a positive reaction; d) an effective amount of a positive control HIT antibody; e) an effective amount of a negative control serum; f) instructions for obtaining normal donor platelets for use in the assay; g) instructions for performing the assay; h) one or more additional reagents such as fluorescent-labeled annexin V or anti-p-selectin antibody to detect markers of platelet activation and g) prostaglandin E1 to minimize baseline platelet activation. Kits with fewer reaction components could comprise: a) an effective amount of purified human PF4; b) an effective amount of at least one labeled anti-human antibody for markers of platelet activation such as anti-human p-selectin antibody and c) instructions for use.

Definitions

By "diagnosing" we mean classifying a pathology (e.g., a cancer or a pre-malignant lesion) or a symptom, determining a severity of the pathology (grade or stage), monitoring pathology progression, and forecasting an outcome of a pathology and/or prospects of recovery.

By "effective amount," we mean an amount of a compound that sufficient to effect the desired outcome. The "effective amount" will vary depending on the compound, the use, the judgment of the attending medical or veterinary practitioner, and other factors.

By "HIT" we mean heparin-induced thrombocytopenia, an adverse reaction to heparin, in which affected patients produce platelet-activating antibodies that bind complexes of platelet-factor 4 (PF4) and heparin, resulting in a pro-thrombotic and thrombocytopenic condition that in severe cases can be life-threatening.

By "heparin-induced" we mean antibodies that result from exposure to heparin or those that recognize PF4 complexed with heparin as in spontaneous HIT, as indicative of HIT.

By "heparin-like compound" we mean a compound with a high negative charge such as a polyanion, a heparin derivative, a chemically modified heparin, a heparin-like glycosaminoglycan molecule, a proteoglycan containing multiple heparin or heparin-like glycosaminoglycans, lower-molecular-weight heparin, or heparin-like glycosaminoglycan any of which could be connected directly or through a spacer/linker molecule to a core molecule.

By "patient" we mean any human having or suspected of having HIT. By "suspected of having HIT" we mean the patient exhibits clinical findings indicative of HIT, including, for example, a below-normal platelet count, enlargement or extension of a previously diagnosed blood clot, or the development of a new blood clot elsewhere in the body. Additional symptoms indicative of HIT include fever, rash, chills, high blood pressure, shortness of breath and chest pain.

By "platelets", also known as thrombocytes, we mean the anucleate fragments of megakaryocytes involved in blood coagulation, hemostasis and blood thrombus formation. Human platelets are routinely isolated through a variety of methods including, but not limited to, platelet apheresis, plateletpheresis and differential centrifugation. Washed normal donor platelets would be suitable, however, platelets from other sources, including unwashed platelets, isolated platelets, or purified platelets, could also be used.

By "platelet activation" we mean the response of platelets when platelets encounter a molecule that triggers activation, such as, for instance, collagen, thromboxane A2, ADP, thrombin and the like. Platelet activation results in various changes to the platelets, including, for example, changes in markers associated with platelet activation, exocytosis of the dense granules and alpha granules, activation of the membrane enzyme phospholipase A2, changes in shape, and more.

Platelet activation levels may be measured using any method known in the art, such as, for instance, measuring levels of a marker found on or released from activated platelets in a patient blood sample as compared to levels of activated platelets in a normal control sample. Any marker known to be found on or released from activated platelets may be used to measure platelet activation, including, for example, one or more CD markers found on activated platelets, including the marker CD62P, also known as p-selectin. In addition, platelet activation can be measured by measuring any increased binding of immunoglobulin, platelet aggregation, intracellular levels of ionized calcium, changes in integrin conformation, release of platelet granule contents, changes in platelet membrane potential or platelet impedance, levels of Fc gamma receptor 2 cleavage fragments, or shape change of platelets.

By "increase in platelet activation", we mean an increase in platelet activation of at least one and a half times that of the baseline platelet activation in a normal blood sample. In one embodiment, the increase in platelet activation is at least two or three times the amount of baseline platelet activation in normal blood samples. Determining an "increase" in a patient blood sample as compared to a normal blood sample may require the use of a test sample, a positive control sample and a known normal sample and statistical methods such as the use of a calculated average, mean, median, or range for the normal sample or samples tested to use for comparison of the test or patient sample.

By "PF4" we mean either native platelet factor 4 (PF4) purified from platelets or recombinant forms of PF4. Native PF4 exists in a tetrameric state. Optimally, PF4 would be tetrameric but other formulations of PF4 could work.

By "sample" we mean a specimen or culture obtained from a human or animal patient suspected of having HIT. Biological samples can be obtained from patients and encompass fluids, solids, tissues, and gases. In one embodiment, the source of the patient antibodies would be serum. However, plasma, whole blood, or other blood products such as platelet-rich plasma and others will be satisfactory. Preferably, a sample of about 0.2 ml is needed for a test reaction. Such examples are not however to be construed as limiting the sample types applicable to the present invention.

By "solid surface" we mean any surface suitable for immobilization of the PF4-heparin complex (or other antigen). The preferred solid support for this technique is polystyrene beads. Other bead types include magnetic beads, microparticles and nanoparticles. Some nanoparticles have a metallic interior. Other solid supports could include ELISA plates made of polystyrene or other plastics.

By "labeled antibodies" we mean any antibody that is labeled with a fluorochrome such as Allophycocyanin (APC)-conjugated AffiniPure F(ab')2 goat anti-human IgG, Fcγ specific, fluoroscein (FITC)-conjugated F(ab')2 goat anti-human IgA, a chain specific, and the like. Additionally, one could use a variety of species for the production of such antibodies including but not limited to mouse, rat, goat, sheep, rabbit, donkey, horse, bovine, porcine, and monkey. These antibodies could be either polyclonal or monoclonal in nature.

By "instructions for use" we mean a publication, a recording, a diagram, or any other medium of expression which is used to communicate the usefulness of the invention for one of the purposes set forth herein. The instructional material of the kit can, for example, be affixed to a container which contains the present invention or be shipped together with a container which contains the invention.

Dilutions. In one embodiment, dilution for patient sample is 1:5 (platelet activation assay) and 1:20 (platelet binding assay). However other dilutions in the range of undiluted to 1:500 may be satisfactory, depending on the needs of the user as determined by one of skill in the art. The most preferred dilution of patient sample used herein is a 1:5-1:20 dilution of serum however other dilutions in the range of 1:2 to 1:10,000, depending on the strength of the antibody response in the patient, can be satisfactory. The most preferred sample type would be serum. However, we predict that whole blood or plasma will be satisfactory. Dilutions above 1:500 may be suitable for samples containing potent antibodies.

Buffers. In a preferred embodiment, PBS-1% BSA or Tyrodes HEPES-1% BSA buffer are used for antibody antigen reactions. However, most isotonic and physiologic solutions known to the art would be satisfactory.

Incubation times. In one embodiment, one would allow the platelet activation and antibody antigen reactions to occur over 5 to 120 minutes and most optimally 60 minutes (platelet binding assay and platelet activation assay). However, longer or shorter incubations could be used as identified by one of skill in the art. Surprisingly, we found that incubations at room temperature and not 37° C. are optimal for measuring both platelet-binding antibodies and platelet-activating antibodies.

Pre-incubation of PF4 with platelets. To measure levels of platelet-binding antibodies and platelet activation, preincubation of PF4 with platelets enhanced assay performance such that SRA-positive and negative samples could be more clearly distinguished. Both the platelet activating assay and platelet binding assay distinguish SRA(−) from SRA(+) antibodies with statistical significance. This is an important practical property of our findings and a preferred embodiment of the invention.

Fluorochromes. In one embodiment, each antibody used in the method of this invention is fluorescently labeled. Any method of fluorescent labeling known to the art may be used, including, for example, using fluorochromes. For instance, in one embodiment, one of skill in the art would use antibodies having emission spectra as non-overlapping as possible, such as, for example, FITC, APC and PE. Substitutions of fluorescently labeled secondary antibodies could be used so that one could distinguish the fluorescent emission of the dye by use of detection lasers present in the flow cytometry equipment. There is no limit to how close the emission spectra of the dyes must be. However, it is generally accepted to look for fluorescently labeled antibodies antibodies that use different lasers for detection.

Flow Cytometry. Flow cytometry is a laser-based, biophysical technology employed in cell counting, sorting, biomarker detection and protein engineering, by suspending cells in a stream of fluid and passing them by an electronic detection apparatus. It allows simultaneous analysis of the physical and/or chemical characteristics of up to thousands of particles per second. Flow cytometry is routinely used in the diagnosis of health disorders, especially blood cancers, but has many other applications in basic research, clinical practice and clinical trials. A common variation is to physically sort particles based on their properties, so as to purify populations of interest. In one embodiment of the invention, flow cytometry, which is capable of detecting and quantifying fluorescently-labeled, cell bound antibodies, is used to detect platelet-activating HIT antibodies by measuring platelet activation (e.g., p-selectin expression) caused by such antibodies or measuring the binding of such antibodies to PF4-treated platelets, thus aiding in the diagnosis of HIT. However, other methods of detecting the fluorescently labeled antibodies known to the art may also be used. For instance, a Luminex type of platform would detect fluorochrome labeled beads or an ELISA plate reader capable of reading fluorescence could also be used.

One of skill in the art would know that various similarly acting materials or conditions can be substituted for those described here. These substitutions could be for the platelets, the platelet specific antigen, the marker of platelet activation, methods of incubating the antibody and antigen mixtures, the range of dilutions used for the antibodies, the buffers used in the reactions, the source of the patient antibodies, the incubation times, the species of the secondary antibodies, the labels used with the secondary antibodies, and the detection format for the labeled antibodies.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention.

Accordingly, the detailed descriptions are to be regarded as illustrative in nature and not restrictive.

III. Examples

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

Example 1: Patients and Clinical Testing

Serum samples (n=53) from patients suspected of having HIT were obtained from the Platelet and Neutrophil Immunology Laboratory of the BloodCenter of Wisconsin (BCW). Samples selected were PF4-ELISA positive with an optical density (OD) >0.4, that decreased >49% with high dose (HD; 100 U/ml) unfractionated heparin (UFH). SRA was performed at least twice on each sample and twenty-nine samples were consistently positive in the serotonin release assay (SRA) and 24 were negative. The research protocol was approved by the Institutional Review Board of BloodCenter of Wisconsin.

Example 2: P-Selectin Assay

Platelets were isolated from citrated platelet-rich plasmas from 2-3 Group 0 blood donors (to minimize inter-donor platelet variability) in the presence of prostaglandin E1. Reaction mixtures consisted of $1 \times 10^6$ platelets in phosphate-buffered saline (PBS)-1% bovine serum albumin (BSA) to which was added (1) 50 μg/ml PF4, (2) 50 μg/ml PF4 and high dose (HD) UFH, or (3) buffer for 20 minutes at room temperature. The amount of PF4 added was optimized to maximize platelet activation in the assay. Ten microliters of serum was then added to produce a final reaction volume of 50 μl. Human PF4 was purified as previously described.

After incubation for 60 minutes at room temperature, phycoerythrin (PE)-labeled p-selectin antibody (BD Biosciences, San Jose, Calif.), and Alexa Fluor 647-labeled anti-GPIIb antibody 290.5 were added. After 15 minutes, the mixture was diluted in 200 μl of PBS-1% BSA and platelet events were acquired in an Accuri C6 flow cytometer. Events were gated by GPIIb positivity and p-selectin PE median fluorescence intensity (MFI) was recorded.

Example 3: Immunoglobulin-Platelet Binding Assay

Platelets were isolated from citrated platelet-rich plasmas from 2-3 Group 0 blood donors (to minimize inter-donor platelet variability) in the presence of prostaglandin E1. Reaction mixtures consisted of $1 \times 10^6$ platelets in phosphate-buffered saline (PBS)-1% bovine serum albumin (BSA) to which was added (1) 50 μg/ml PF4, (2) 50 μg/ml PF4 and high dose (HD) UFH, and (3) buffer for 20 minutes at room temperature. The amount of PF4 added was optimized to maximize IgG binding to platelets in the assay. 2.5 microliters of serum was then added to a final reaction volume of 50 μl. After incubation for 60 minutes at room temperature, FITC-labeled goat anti-human IgG antibody (Jackson Immunoresearch, West Grove, Pa.), and Alexa Fluor 647-labeled anti-GPIIb antibody 290.5 were added. After 30 minutes, the mixture was diluted in 200 μl of PBS-1% BSA and platelet events were acquired in an Accuri C6 flow cytometer. Events were gated by GPIIb positivity and anti-human IgG FITC median fluorescence intensity (MFI) was recorded.

Statistics: The Mann Whitney test was used to compare the two groups of SRA+ and SRA− samples (Prism, Graphpad, La Jolla, Calif.). Receiver operating characteristic curves were constructed using Analyse-it software (Leeds, UK). A p value of <0.05 was considered significant.

Results

SRA-positive, but not SRA-negative patient samples, induced platelet p-selectin expression in platelets pre-treated with PF4. The ability of the 53-member HIT antibody panel to induce p-selectin expression in platelets pre-treated with PF4 was characterized. As shown in FIG. 1A (left), when untreated platelets were used, SRA-negative samples failed to induce p-selectin expression and SRA-positive samples produced only a slight, but significant p-selectin increase (average increase in median fluorescence intensity (MFI) of 2295 vs. −112 relative to normal serum, p<0.0001 for SRA+vs. SRA− samples, respectively).

When platelets pre-treated with PF4 were used in the assay, p-selectin expression induced by the SRA-positive samples, but not the SRA negative samples, was greatly augmented (FIG. 1A, center; average increase in median fluorescence intensity (MFI) of 12,037 vs. 1415 relative to normal serum, p<0.0001 for SRA+vs. SRA− samples, respectively). p-selectin expression was significantly inhibited by high dose heparin (FIG. 1A, right).

Figure 1B:
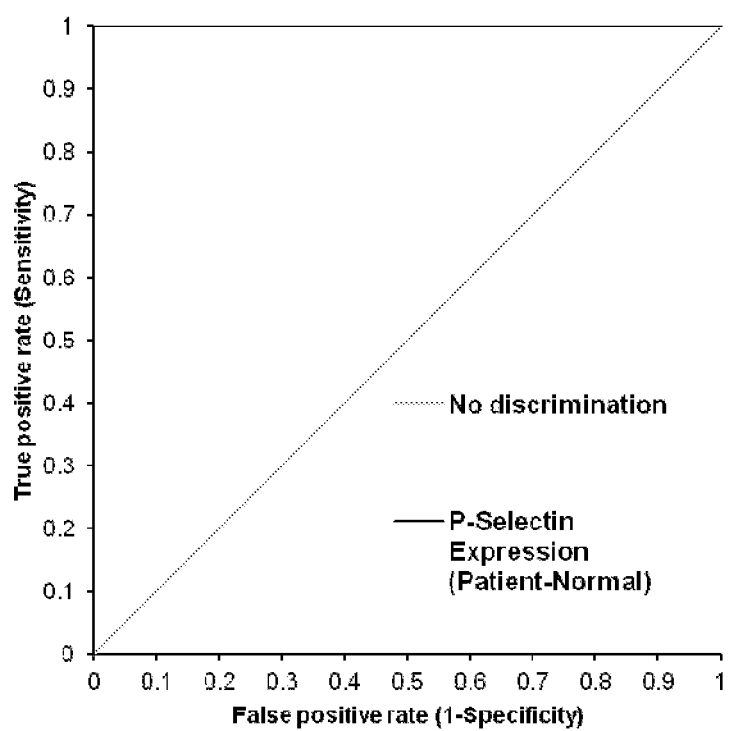

In ROC analysis, area under the curve (AUC) provides a measure of diagnostic accuracy. The p-selectin expression assay attained a perfect AUC measurement of 1.0 (FIG. 1B). This suggests that the p-selectin expression assay can be used as a surrogate for the SRA with a very high degree of confidence. As used herein the terms "PF4-fortified p-selectin release assay", "p-selectin expression assay", and "platelet activation assay" all refer to the method of the subject invention.

Antibodies in SRA(+) but not SRA(−) patient sera recognized platelets pre-treated with PF4. As shown in FIG. 2A (left) IgG from SRA-negative samples failed to bind to untreated platelets and SRA-positive samples produced only a slight, but significant increase in IgG binding (average increase in median fluorescence intensity (MFI) of 5,046 vs. 2,665 relative to normal serum, p<0.05 for SRA+vs. SRA− samples, respectively).

In contrast, antibodies in most SRA(+) patient samples but not SRA(−) samples did recognize platelets pre-treated with PF4. (FIG. 2A, center; average increase in median fluorescence intensity (MFI) of 29,585 vs. 3,393 relative to normal serum, p<0.0001 for SRA+ vs. SRA− samples, respectively). IgG binding to platelets was significantly inhibited by high dose heparin (FIG. 2A, right).

Figure 2B:
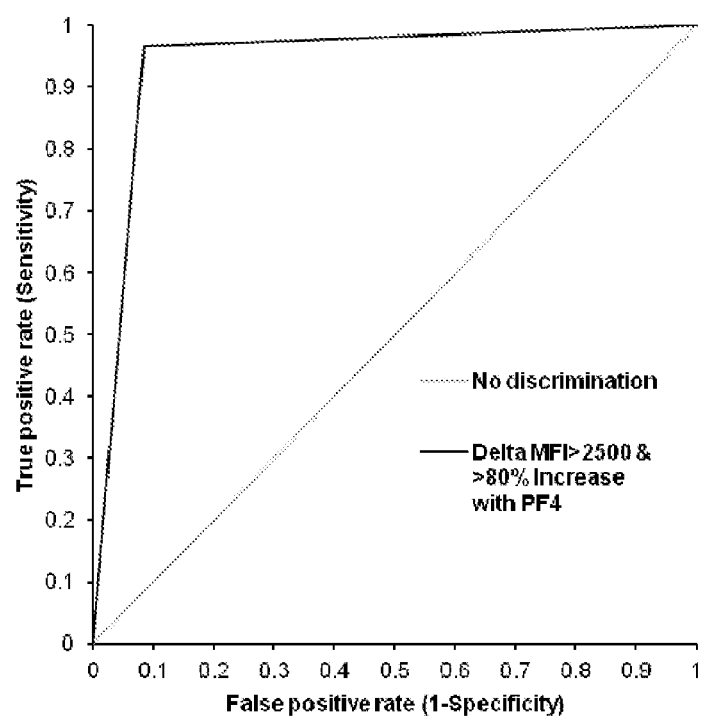

The platelet binding assay attained an AUC measure of 0.94 (FIG. 2B). This suggests that the platelet binding assay of the present invention can be used as a surrogate for the SRA with a high degree of confidence. As used herein the terms "PF4-fortified platelet binding assay", "IgG-platelet binding assay", and "immunoglobulin-platelet binding assay" all refer to the subject invention.

The above description, attached figures, and claims listed below are intended to be illustrative and not limiting of this invention. In light of the invention described herein, many themes and variations to this invention will be suggested to one skilled in the art. All such themes and variations are within the contemplation hereof. For instance, while this invention has been described in conjunction with the various exemplary embodiments outlined above and in the below claims, various alternatives, modifications, variations, improvements, and/or substantial equivalents, whether known or that rare or may be presently unforeseen, may become apparent to those having at least ordinary skill in the art. Various changes may be made without departing from the spirit and scope of the invention. Therefore, the invention is intended to embrace all known or later-developed alternatives, modifications, variations, improvements, and/or substantial equivalents of these exemplary embodiments.

REFERENCES

1. Jang I K, Hursting M J. Circulation. 2005; 111:2671-2683.
2. Arepally G M, Ortel T L. Annu Rev Med. 2010; 61:77-90.
3. Shantsila E, Lip G Y, Chong B H. Chest. 2009; 135:1651-1664.
4. Lo G K, Sigouin C S, Warkentin T. Am J Hematol. 2007; 82:1037-1043.
5. Warkentin T E, Levine M N, Hirsh J, et al. N Engl J Med. 1995; 332:1330-1335.
6. Warkentin T E. Hematology Am Soc Hematol Educ Program. 2011; 2011:143-149.
7. Amiral J, Bridey F, Dreyfus M, et al. Thromb Haemost. 1992; 68:95-96.
8. Visentin G P, Ford S E, Scott J P, Aster R H. J Clin Invest. 1994; 93:81-88.
9. Kelton J G et al. Blood. 1994; 83:3232-3239.
10. Greinacher A et al. Thromb Haemost. 1994; 71:247-251.
11. Greinacher A, Juhl D, Strobel U, et al. J Thromb Haemost. 2007; 5:1666-1673.
12. Bakchoul T et al. Thromb Res. 2011; 127:345-348.
13. Morel-Kopp M C et al. Int J Lab Hematol. 2010; 33:245-250.
14. Juhl D et al. Eur J Haematol. 2006; 76:420-426.
15. Cuker A, Rux A H, Hinds J L, et al. Blood. 2013; 121:3727-3732.
16. Nazi I, Arnold D M, Smith J W, et al. J Thromb Haemost. 2013; 11:1146-1153.
17. Levine R L. Chest. 2005; 127:1488-1490.
18. Davoren A, Aster R H. Am J Hematol. 2006; 81:36-44.
19. U.S. Cancer Statistics Working Group. http://www.cdc.gov/uses.
20. Go A S, Mozaffarian D, Roger V L, et al. Circulation. 2013; 127:e6-e245.
21. Cuker A, Cines D B. Blood. 2012; 119:2209-2218.
22. McFarland J et al. Am J Hematol. 2012; 87:776-781.
23. Sheridan D, Carter C, Kelton J G. Blood. 1986; 67:27-30.
24. Bougie D W et al. Blood. 2010; 116:3033-3038.
25. Bougie D W, Rasmussen M, Zhu J, Aster R H. Blood. 2012; 119:6317-6325.
26. Zou K H, O'Malley A J, Mauri L. Circulation. 2007; 115:654-657.
27. Rauova L et al. Blood. 2006; 107:2346-2353.
28. Newman P M, Chong B H. Blood. 2000; 96:182-187.
29. Horne M K, 3rd, Alkins B R. J Lab Clin Med. 1996; 127:435-442.
30. Horne M K, 3rd, Hutchison K J. Am J Hematol. 1998; 58:24-30.
31. Suh J S, Aster R H, Visentin GPBlood. 1998; 91: 916-22.
32. U.S. Pat. No. 5,763,201 to Aaron Tomer.
33. Sachais B S et al. Blood. 2012 Aug. 2; 120(5):1137-42.
34. Kowalska M A et al. Blood. 2011 Sep. 8; 118(10):2882-8.
35. Rauova L et al. Blood. 2010 Dec. 2; 116(23):5021-31.
36. Kowalska M A et al. Thromb Res. 2010 April; 125(4):292-6.
37. Rauova L et al. J Thromb Haemost. 2009 July; 7 Suppl 1:249-52.
38. Poncz M et al. Pathophysiol Haemost Thromb. 2006; 35(1-2):46-9.
39. Suvarna S et al. Blood. 2005 Aug. 1; 106(3):929-31.

We claim:

1. A kit for determining the presence of platelet-activating pathogenic heparin-induced thrombocytopenia (HIT) antibodies as opposed to non-activating non-pathogenic HIT antibodies in a whole blood, plasma or serum sample from a patient suspected of having HIT comprising:
    a) purified platelet factor 4 (PF4);
    b) an antibody or probe capable of detecting platelet activation or antibody bound to platelets;
    c) instructions for use;
    d) an effective amount of whole blood, plasma, or serum control sample negative for platelet-activating pathogenic HIT antibodies; and
    e) an effective amount of whole blood, plasma, or serum control sample positive for platelet-activating pathogenic HIT antibodies.

2. The kit of claim 1 further comprising at least 50 U/ml of heparin.

3. The kit of claim 1 further comprising an inhibitor of platelet activation.

4. The kit of claim 3 wherein the inhibitor of platelet activation is prostaglandin E1.

5. The kit of claim 1 wherein the antibody or probe is fluorescently labeled.

6. The kit of claim 5 wherein the antibody or probe is fluorescent-labeled annexin V.

7. The kit of claim 5 wherein the antibody or probe is fluorescent-labeled anti-p-selectin antibody.

* * * * *